(12) United States Patent
Rani et al.

(10) Patent No.: US 11,675,215 B1
(45) Date of Patent: Jun. 13, 2023

(54) EYEGLASS SYSTEMS

(71) Applicant: Amazon Technologies, Inc., Seattle, WA (US)

(72) Inventors: Neelam Rani, Sunnyvale, CA (US); Sakthi Ramanathan Sivaraman, Santa Clara, CA (US)

(73) Assignee: Amazon Technologies, Inc., Seattle, WA (US)

( * ) Notice: Subject to any disclaimer, the term of this patent is extended or adjusted under 35 U.S.C. 154(b) by 388 days.

(21) Appl. No.: 16/854,391

(22) Filed: Apr. 21, 2020

(51) Int. Cl.
| | |
|---|---|
| *G02C 7/08* | (2006.01) |
| *G06F 1/26* | (2006.01) |
| *G06T 7/50* | (2017.01) |
| *G06T 7/60* | (2017.01) |
| *G06V 40/18* | (2022.01) |
| *G16H 10/60* | (2018.01) |

(52) U.S. Cl.
CPC .............. *G02C 7/081* (2013.01); *G06F 1/266* (2013.01); *G06T 7/50* (2017.01); *G06T 7/60* (2013.01); *G06V 40/18* (2022.01); *G06T 2207/30041* (2013.01); *G06T 2207/30201* (2013.01); *G16H 10/60* (2018.01)

(58) Field of Classification Search
CPC ... G06T 7/50; G06T 7/60; G06T 2207/30041; G06T 2207/30201; G06F 1/266; G06F 3/013; G06V 40/18; G02C 7/081; G02B 2027/0174; G02B 2027/0178; G02B 2027/0127; G02B 2027/0187; G02B 27/0093
See application file for complete search history.

(56) References Cited

U.S. PATENT DOCUMENTS

| | | | | |
|---|---|---|---|---|
| 10,901,205 | B1* | 1/2021 | Lu | G02B 27/017 |
| 10,901,291 | B1* | 1/2021 | Sulai | G02B 3/10 |
| 2015/0185503 | A1* | 7/2015 | Tate | G02C 7/083 |
| | | | | 351/159.01 |
| 2020/0033666 | A1* | 1/2020 | Li | G02B 5/1876 |
| 2020/0233214 | A1* | 7/2020 | Jia | H04N 13/344 |
| 2021/0026045 | A1* | 1/2021 | Jacoby | G02C 7/085 |
| 2022/0100000 | A1* | 3/2022 | Guillot | G02C 7/028 |

* cited by examiner

*Primary Examiner* — Jin Cheng Wang
(74) *Attorney, Agent, or Firm* — Lee & Hayes, P.C.

(57) ABSTRACT

This disclosure describes, in part, eyeglass systems configured to automatically adjust an optical-power value, or optical power, of lenses of the eyeglass system based on the distance between eyes of a user wearing the eyeglass system and an object that the user is looking at. In some instances, the eyeglass system may determine a degree-of-convergence (DoC) or convergence angle between the left eye and the right eye of the user to determine the distance between the eyes of the user and the object the user is viewing. Further, the eyeglass system may include a power source and lenses that change their optical-power value based on different voltage or current values provided to the lenses by the power source.

20 Claims, 12 Drawing Sheets

602

$RATIO_1 = D_1 / D_2$ $RATIO_2 = D_3 / D_4$ $RATIO_3 (DoC) = RATIO_1 / RATIO_2$

IF:
    $1.0 < R_3 < 1.1$, THEN SET REFRACTIVE-INDEX VALUE$_1$ $1.1 < R_3 < 1.3$, THEN SET REFRACTIVE-INDEX VALUE$_2$ $R_3 > 1.3$, THEN SET REFRACTIVE-INDEX VALUE$_3$

CALCULATION COMPONENT 330

FIG. 6

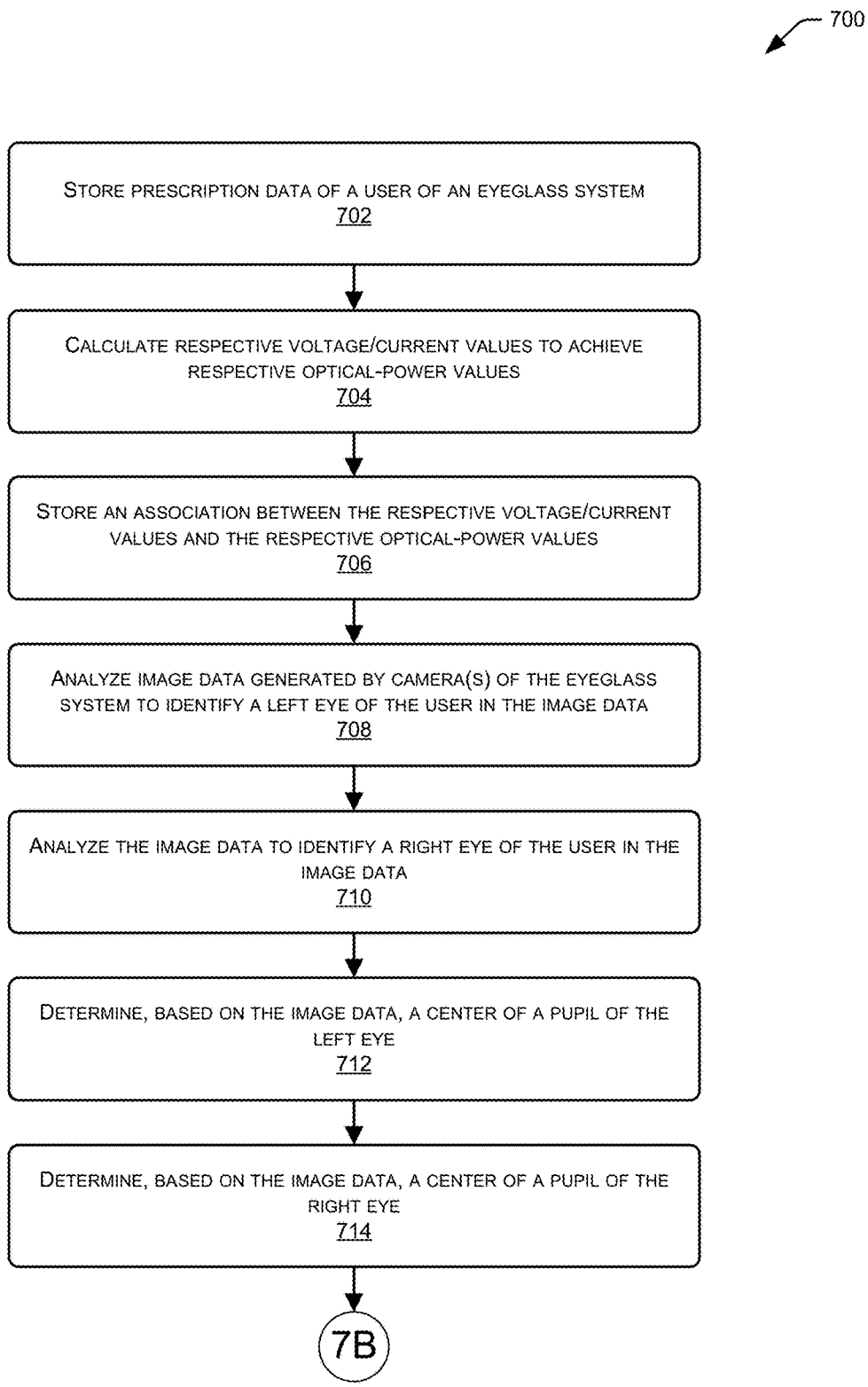

EYEGLASS SYSTEMS

BACKGROUND

Many people rely on eyeglasses to aid their vision and help them more clearly see objects at a distance, up close, or both. For example, some people use bifocals, which are eyeglasses that include a first portion of the lens having a first optical power for seeing distant objects, and a second portion of the lens having a second optical power for viewing objects up close. In other instances, some people use trifocals, which include three distinct optical powers. While these types of eyeglasses are helpful, one downside is that each respective portion of these lenses have a fixed optical power and, thus, people may struggle adapting to the need to look through the appropriate portion of the lenses depending on the type of object a person is currently viewing.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

FIG. 6 illustrates an example component of the eyeglass system that may use the measurements determined by the components of FIG. 5 for determining a DoC of the eyes of the user for determining a desired optical-power value. After determining a desired optical-power value, the eyeglass system may identify a voltage or current level to apply to lenses to achieve this optical-power value.

FIGS. 7A-C collectively illustrate a flow diagram of an example process for automatically changing an optical power index of lenses of an eyeglass system based on a current DoC of the eyes of a user wearing the eyeglass system.

DETAILED DESCRIPTION

Figure 1:
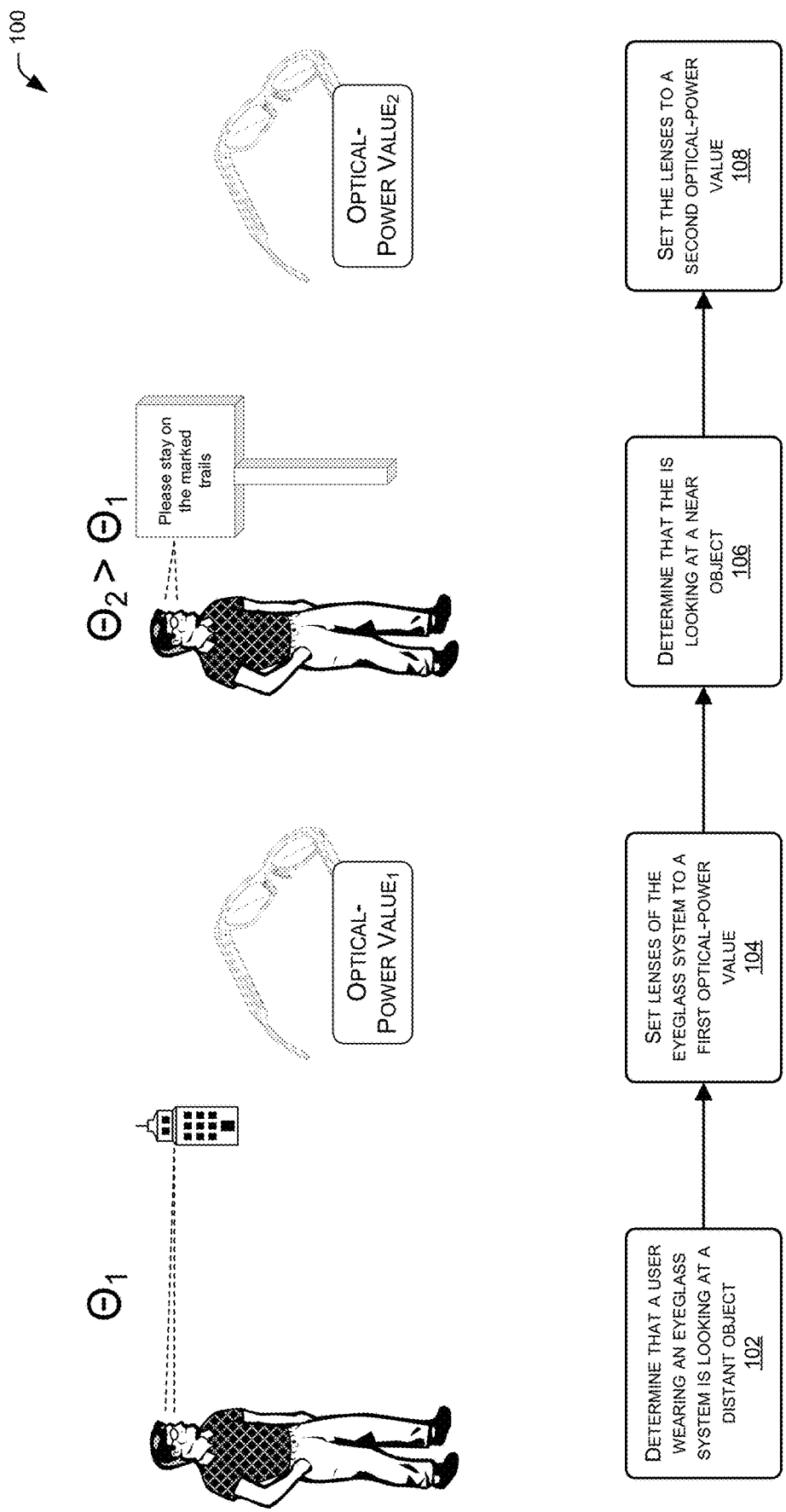
FIG. 1 illustrates an example process in which an eyeglass system determines whether a user wearing the eyeglass system is looking at a distant object or a near object and changes optical power of the lenses of the eyeglass system in response.

This disclosure describes, in part, an eyeglass system configured to automatically adjust an optical-power value, or optical power, of lenses of the eyeglass system based on the distance between a user wearing the eyeglass system and an object that the user is looking at. In some instances, the eyeglass system may determine a degree-of-convergence (DoC) or convergence angle between the left eye and the right eye of the user to determine the distance between the eyes of the user and the object the user is viewing. Further, the eyeglass system may include a power source and lenses that change their optical-power value based on different voltage or current levels applied to the lenses by the power source (e.g., liquid-crystal lenses, liquid lenses, etc.).

In some examples, eyeglass system includes a frame and left and right lenses, similar to traditional prescription eyeglasses. In some instances, however, the focal length of the lenses may be adjustable. For example, the lenses may comprise liquid-crystal (LC) lenses that includes an LC layer between two substrates that attach to one or more electrodes that electrically connect to a power source coupled to (e.g., within, on the outside of, etc.) the frame of the glasses. When the power source applies different voltage or current levels, the resulting electrical field may manipulate the LC layer. For example, applying the voltage or current may change the optical power of these LC lenses, the resulting optical-power value depending upon the applied voltage or current level. For example, the relationship between the focal length of the lenses and the applied voltage or current may be as follows:

$$f_{GRIN} = \frac{r^2}{2 \times t \times (n_{max} - n(r))}$$

where:

$f_{GRIN}$ = focal length, which is equal to $\frac{1}{\text{Diopeter Power(Sphere value)}}$ $r$ = radius of the lens(fixed)

$t$ = thickness of the lens(fixed)

$n_{max}$ = maximum refractive index at optical axis of each lens(fixed)

(e.g., refractive index of the subtrates)

$n(r)$ = refractive index at position $r$, which has a relation, based on lens specs, -continued to voltage (V) or current to be applied to the LC to acheive a focal length($f_{GRIN}$)GRIN(gradient index lens) = the design of the LC for adaptive purpose(e.g., based on gradual variation of the refractive index without necessity of curved surfaces, using the birefringence property of liquid crystals In other instances, the lenses described herein may comprise "Liquid Lenses" that alter their focal length without a mechanical part. Instead, these lenses utilize electrowetting techniques. The lenses may comprise a sealed cell, such as two substrates containing an oil and water. As is known, the electrowetting process may shape the oil drop differently based on different amounts of electrical current applied to the lens. That is, a first amount of current may shape the oil in a first manner, a second amount of current in a second manner, and so forth. These different shapes may result in a different optical power of the lenses. Therefore, the lens specifications may indicate the a mapping or other indication of amount of current to focal power, which the eyeglass system may use to tune the optical power of the lenses, as described herein.

In some instances, the eyeglass system may be configured with prescription data indicating an optical prescription associated with a user of the eyeglass system. For example, the user may input the prescription data into a computing device (e.g., mobile phone, laptop, etc.) of the user, which may communicate the prescription data to the eyeglass system. For example, the user may capture an image of a prescription and upload the image to an application stored on a mobile device, which may perform image and character recognition to identify the prescription data. In another example, the user may use an application to manually (e.g., using a keyboard, audibly, etc.) input the prescription data into the application. After the application receives the prescription data, the device may then send this prescription data to the eyeglass system. The eyeglass system may then use the prescription data and the equation described above to determine the voltage or current levels to apply to lenses of the eyeglass system to achieve the different optical-power values specified in the prescription data. In other instances, meanwhile, the mobile device or other device of the user may use the equation above to determine the voltage or current levels for achieving the desired optical-power values and may provide these voltage or current levels (in association with each level's corresponding optical-power value) to the eyeglass system, which may store this information).

Given the prescription data and the equation above, the eyeglass system and/or another device may calculate the needed voltage or current values to apply to the lenses to achieve the different optical-power values. In some instances, the prescription data corresponds to bifocal prescription data, which case the eyeglass system is configured to apply either a first voltage or current level to achieve a first optical-power value (e.g., for looking at near objects within fourteen inches of the eyes user) or a second voltage or current level to achieve a second optical-power value (e.g., for looking at all other objects). In another example, the prescription data corresponds to trifocal prescription data, which case the eyeglass system is configured to apply either a first voltage or current level to achieve a first optical-power value (e.g., for looking at near objects within fourteen inches of the eyes user), a second voltage or current level to achieve a second optical-power value (e.g., for looking at mid-range objects between fourteen and thirty-six inches from the eyes of the user), or a third voltage or current level to achieve a third optical-power value (e.g., for looking at distant objects beyond thirty-six inches from the eyes of the user). In still other instances, meanwhile, the eyeglass system may apply any other number of voltage or current values for achieving any other number of optical-power values. Further, in some instances the eyeglass system might not store the prescription data, but instead may receive one or more tables or other data structures that indicate different voltages or currents to apply to the lenses in order to achieve different optical powers. In some instances, each table may be associated with a particular temperature range, such that the eyeglass system may reference the appropriate table based on a current ambient temperature, which may be determined by a temperature sensor coupled to the lenses or frame of the eyeglass system.

In order to apply the appropriate voltage or current level to achieve the appropriate optical-power value at any given time, however, the eyeglass system may be configured to determine information indicative of a distance between the eyes of the user and an object that the user is currently looking at. That is, the eyeglass system may include functionality for determining whether the user is looking at a distant object, a mid-range object, a near object, or the like. Based on this information, the eyeglass system may apply the appropriate voltage or current level to achieve the desired optical-power value.

In some instances, the eyeglass system may use information indicating a degree-of-convergence (DoC), or convergence value, between the left eye and the right eye of the user as indicative of the distance between the eyes of the user and the object upon which the user sets their gaze. As is known, when a user looks at a distant object, the optical axis of the left eye of the user may be generally parallel to the optical axis of the right eye of the user. Thus, the convergence angle may be relative small. When the user looks at a closeup object, such as a book they are reading, however, these two optical axes will be more greatly directed towards one another. Stated otherwise, the convergence angle between these two optical axes may be larger than when the user is looking at a distant object.

The eyeglass system, therefore, may be configured to use this information to determine the distance between the user's eyes and the object upon which they gaze. In the bifocal example, for instance, this information may be used to determine whether the user is looking at a distant object or at a near object and may apply the appropriate voltage or current level based on this determination. In the trifocal example, meanwhile, this information may be used to determine whether the user is looking at a distant object, a mid-range object, or a near object and may apply the appropriate voltage or current level based on this determination. Again, the eyeglass system may also be configured to make any other similar type of determination.

In some instances, the eyeglass system includes one or more sensors for generating sensor data, which the eyeglass system or another device may analyze to determine the distance described above and, hence, the appropriate voltage or current level. In some examples, the eyeglass system includes functionality for analyzing this sensor data and determining the voltage or current level, while in other instances the eyeglass system provides this sensor data to another device (e.g., a mobile phone of the user, a remote server, etc.) for analyzing the sensor data and making the determination regarding the appropriate voltage or current level.

In some examples, the sensors may comprise one or more cameras configured to generate image data. For example, the sensor may comprise a single camera mounted in such a way to have a field-of-view (FOV) of both eyes of the user and, thus, configured to generate image data of both eyes. In other instances, the sensors may comprise a first camera having an FOV of a left eye of the user and a second camera having an FOV of the right eye of the user. For example, the eyeglass system may include the first camera mounted on a top portion of the frame in which the left lens couples and the second camera mounted on a top portion of the frame in which the right lens couples. In still other instances, the camera may couple to or comprise a portion of each respective lens. Of course, while a few examples are described, it is to be appreciated that the cameras may couple in any other manner.

Regardless of the configuration of the camera(s), the eyeglass system, or another device, may analyze the image data to determine position of the eyes of the user for determining the voltage or current level to apply to the lenses. In some instances, the eyeglass system may use one or more computer-vision techniques to first identify the location of the left eye and the location of the right eye in the image data. For example, the eyeglass system or another device may analyze first image data using a machine-learned model to identify a portion of the first image data that depicts the left eye of the user. Similarly, the eyeglass system or other device may analyze second image data using a machine-learned model to identify a portion of the second image data that depicts the right eye of the user. In some instances, this machine-learned model identifies the respective eyes based on landmarks around each eye, the shape of the eye, the color of the eye relative to the surrounding skin, and/or the like.

Upon identifying each eye, the eyeglass system or another may also use the respective image data to identify a pupil of the left eye and a pupil of the right eye. For example, the eyeglass system or another device may apply binary gradient thresholding to classify each pixel of the image data as either black or white. For example, the eyeglass system or the other device may determine which pixels of image data are darker than a predefined value, such as 128, 200, or the like, where zero (0) represents black and 256 represents white. Stated otherwise, given that the pupil is the darkest portion of the human eye, the gradient-thresholding techniques may identify the darkest part of the eye, which corresponds to the pupil. After identifying the pupil of the left eye, the eyeglass system or the other device may also analyze the second image data corresponding to the right eye. Again, the eyeglass system or the other device may use the gradient-thresholding techniques to identify the pupil of the right eye. Of course, while the above example describes one technique for identify the location of the pupils, other techniques may also be used. In addition, while the above example describes respective image data for the left and right eyes, in other instances the same image data may be operated upon.

After identifying the locations of each eye and the locations of respective pupils within the image data, the eyeglass system or the other device may perform one or more measurements for determining a DoC or convergence angle between the user's eyes, which in turn may be used to determine a voltage or current level to apply to the lenses (for causing the lenses to exhibit a desired optical-power value). In one example, the eyeglass system or the other device determines a first distance between a first edge (e.g., a left edge) of the left eye and a center of a pupil of the left eye, as well as a second distance between the first edge of the left eye and a second edge (e.g., a right edge) of the left eye. In addition, the eyeglass system or the other device may determine a third distance between the first edge (e.g., the left edge) of the right eye and a center of a pupil of the right eye, as well as a fourth distance between the first edge of the right eye and the second edge (e.g., the right edge) of the right eye.

After determining these distances, the eyeglass system or the other device may calculate a first ratio comprising a ratio between the first distance and the second distance. In addition, the eyeglass system or the other device may calculate a second ratio comprising a ratio between the third distance and the fourth distance. Finally, the eyeglass system or the other device may calculate a third ratio comprising a ratio between the first ratio and the second ratio.

As the reader will appreciate, when the user is looking at a distant object, and thus the optical axes of the eyes of the user are generally parallel, the third ratio may be approximately one (e.g., between 0.9 and 1.1 or between 0.95 and 1.05). When, however, the user is looking at a near object, and thus the optical axes are directed somewhat towards each other, the third ratio may be greater than one. Therefore, the eyeglass system or the other device may be configured to map this third ratio, representing the DoC of the eyes of the user, to a voltage or current level that will result in the appropriate optical-power value. For example, if a particular value of the third ratio (e.g., approximately one, 1.0 to 1.1, etc.) indicates that the user is looking at a distant object, then the eyeglass system or the other device may be configured to apply a voltage or current level that results in an optical-power value of the lens specified in the prescription data of the user for viewing distant objects. If, however, the value of the third ratio (e.g., greater than 1.1) indicates that the user is looking at a mid-range or near object, then the eyeglass system or the other device may be configured to apply a voltage or current level that results in an optical-power value of the lens specified in the prescription data for the user for viewing mid-range or near objects. Of course, while this example describes two optical-power values for the example of bifocals, in other instances a greater number of optical-power values (and, thus, voltage or current levels) may applied. For example, in the trifocal example, the eyeglass system or the other device may be configured to apply a first optical-power value for a DoC of 1.0 to 1.1, a second optical-power value for a DoC of 1.1 to 1.3, and a third optical-power value for a DoC of greater than 1.3 Further, while the above example describes example DoC values, it is to be appreciated that other measurements, ratios, thresholds, and the like the may be utilized for determining the appropriate voltage or current level to apply to the lenses at any given time.

Further, in some instances, the eyeglass system may apply different voltage or current levels to the left and right lenses for causing these lenses to have different optical powers. For example, if a user's prescription indicates that the right lens is to have a first optical power and the second lens is to have a second optical power, then the eyeglass system may apply a first voltage or current level to the first lens and a second optical power to the second lens to achieve these different optical powers.

Certain implementations and embodiments of the disclosure will now be described more fully below with reference to the accompanying figures, in which various aspects are shown. However, the various aspects may be implemented in many different forms and should not be construed as limited to the implementations set forth herein. The disclosure encompasses variations of the embodiments, as described herein. Like numbers refer to like elements throughout.

FIG. 1 illustrates an example process 100 in which an eyeglass system described herein, and/or another device, determines whether a user wearing the eyeglass system is looking at a distant object or a near object and changes an optical-power value, or "optical power", of the lenses of the eyeglass system in response. In some instances, the eyeglass system worn by the user performs some or all of the operations, while in other instances another device, such as a mobile phone or a remote server, may communicatively couple to the eyeglass system and perform some or all of the operations.

An operation 102 represents determining that the user wearing the eyeglass system is looking at a distant object. In this example, the user is looking at a building in the distance, resulting in a convergence angle, $\Theta_1$, that is relatively small and approaching zero. In some instances, the eyeglass system 102 or another device may determine that the user is looking at the distant object based on analyzing sensor data generated by one or more sensors of the eyeglass system, such as image data generated by one or more cameras mounted to a frame of the eyeglass system. In some of these instances, the eyeglass system or the other device may determine that the user is looking at the distant object using the techniques described below with reference to FIGS. 2-10.

An operation 104, meanwhile, represents setting lenses of the eyeglass system to a first optical-power value, which may comprise a value that is associated with viewing distant objects. In some instances, this operation may comprise instructing a power source onboard the eyeglass system to apply a first voltage or current level to the lenses to manipulate the physical properties of the lenses to exhibit the first optical-power value. Further, the eyeglass system may access a datastore, onboard the eyeglass system or stored on another device, that associates the viewing of distant objects with the first voltage or current level. The operation 104 may be performed using some or all of the techniques described below with reference to FIGS. 2-10.

Next, an operation 106 represents determining that the user is looking a near object, such as the illustrated sign. In some instances, a near object may comprise an object that is within twelve inches of the eyes of the user, two feet of the eyes of the user, or the like. As illustrated, because the user's eyes are viewing the near object, the convergence angle, $\Theta_2$, may be greater than the convergence angle, $\Theta_1$ associated with the user viewing the distant object. Again, the eyeglass system or the other device may determine that the user is looking at the distant object using the techniques described below with reference to FIGS. 2-10.

Finally, an operation 108 represents setting lenses of the eyeglass system to a second optical-power value, which may comprise a value that is associated with viewing near objects. In some instances, this operation may comprise instructing a power source onboard the eyeglass system to apply a second voltage or current level to the lenses to manipulate the physical properties of the lenses to exhibit the second optical-power value. Further, the eyeglass system may access the datastore, onboard the eyeglass system or stored on another device, that associates the viewing of near objects with the second voltage or current level. The operation 108 may be performed using some or all of the techniques described below with reference to FIGS. 2-10.

Figure 2:
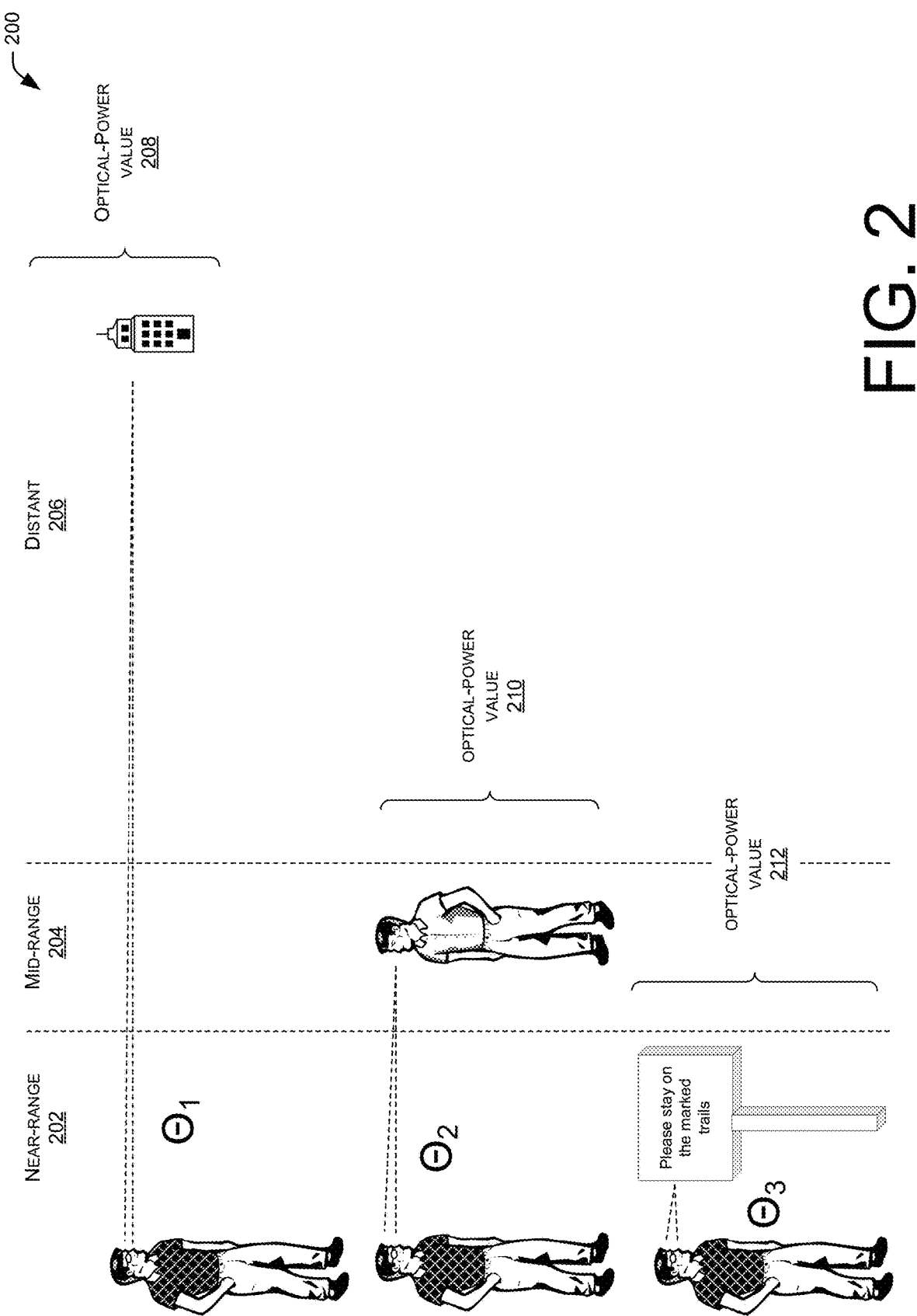
FIG. 2 illustrates an example scenario where an eyeglass system is configured to cause lenses of the eyeglass system to change to different optical-power values based at least in part on different convergence angles of left and right eyes of the user and, hence, based on whether the user is viewing a distant, mid-range, or near object.

FIG. 2 illustrates an example scenario 200 where an eyeglass system is configured to cause lenses of the eyeglass system to change to different optical-power values based at least in part on different convergence angles of left and right eyes of the user and, hence, based on whether the user is viewing a distant, mid-range, or near object. For example, the scenario 200 indicates that, for any given time, a user may be determined to be looking in a near-range object 202, a mid-range object 204, or a distant object 206, such as in the example where the eyeglass system operates as trifocals. As illustrated, the eyeglass system may be configured to set different respective optical-power values to lenses of the eyeglass system based on whether the user is determined to be looking at an object in the near-range 202, the mid-range 204, or the distant-range 206.

For example, the eyeglass system may be configured change an optical power of the lenses of the eyeglass system to an optical-power value 208 in response to determining that the user is looking at an object in the distant range 206, an optical-power value 210 in response to determining that the user is looking at an object in the mid-range 204, and an optical-power value 212 in response to determining that the user is looking at an object in the near-range 202. In some instances, the near-range 202 may comprise zero to twelve inches away from the eyes of the user, the mid-range 204 may comprise twelve inches to thirty-six inches away from the eyes of the user, and the distant-range 206 may comprise beyond thirty-six inches away from the eyes of the user. Of course, in other instances the ranges may have other values. Further, while FIG. 2 illustrates three example ranges and corresponding optical-power values, in other instances the eyeglass system may utilize any other number of ranges (or a continuous range) and corresponding optical-power values, such as in instances where the eyeglass system operates as bifocals and, thus, utilizes a first optical-power value for distant objects and a second optical-power value for near objects.

Figure 3:
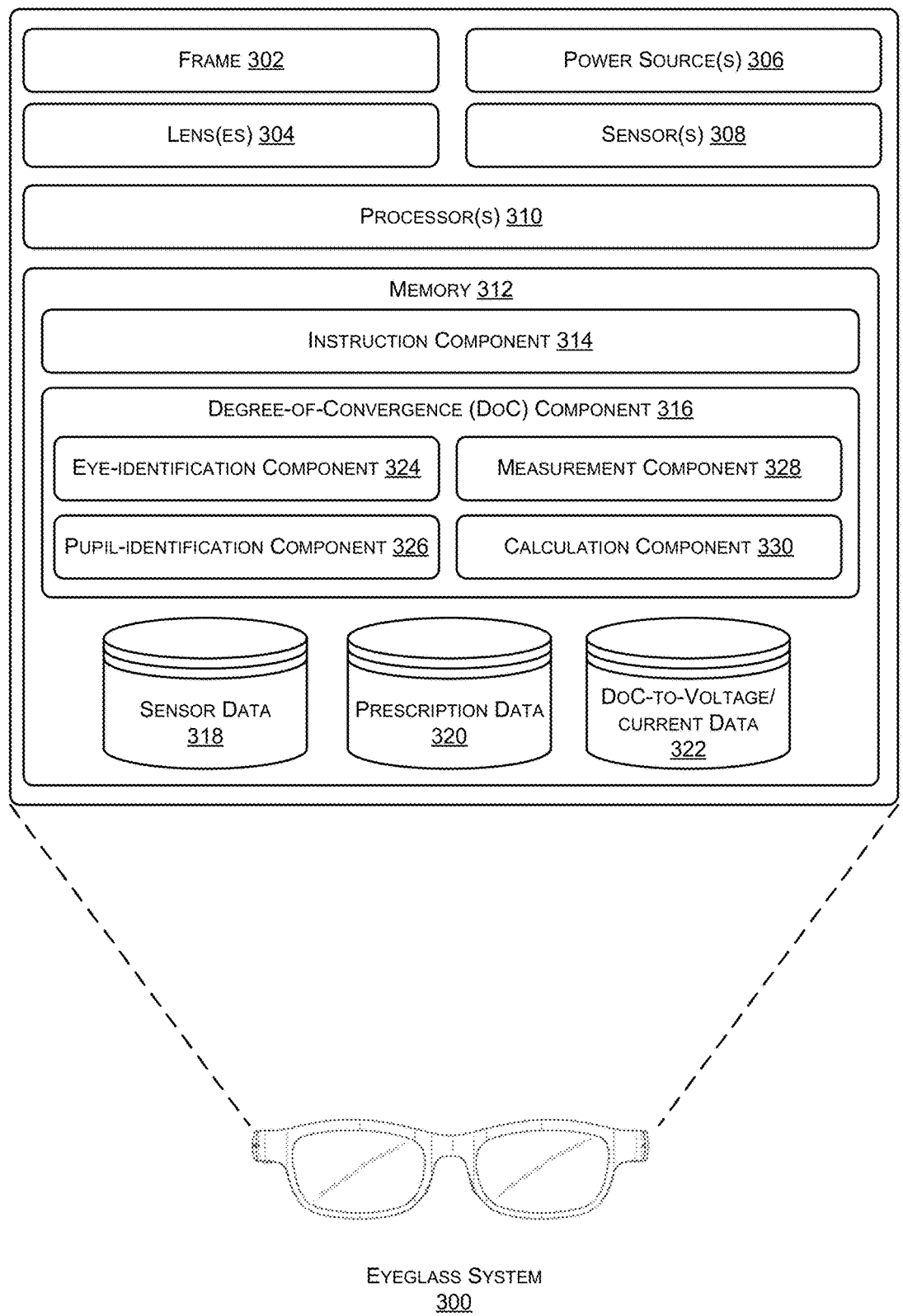
FIG. 3 illustrates example components of eyeglass systems configured to automatically adjust an optical power of lenses of the eyeglass system based on where a user is currently looking.

FIG. 3 illustrates example components of an eyeglass system 300 configured to automatically adjust an optical power of lenses of the eyeglass system based on where a user is currently looking. As illustrated, the eyeglass system 300 may include a frame 302, one or more lenses 304 (e.g., a left lens and a right lens) coupled to the frame 302, one or more power sources 306 for applying varying voltage or current levels to the lenses 304 to adjust an optical power of the lenses 304, and one or more sensors 308. As noted above, the lenses 304 may comprise liquid-crystal (LC) lenses that includes an LC layer between two substrates that attach to one or more electrodes that electrically connect to a power source coupled to (e.g., within, on the outside of, etc.) the frame of the glasses. When the power source applies different voltage or current levels, the resulting electrical field may manipulate the LC layer. For example, applying the voltage or current may change the optical power of these LC lenses, the resulting optical-power value depending upon the applied voltage or current level. For example, the relationship between the focal length of the lenses and the applied voltage or current may be as follows:

$$f_{GRIN} = \frac{r^2}{2 \times t \times (n_{max} - n(r))}$$

where:

$f_{GRIN}$ = focal length, which is equal to $\frac{1}{\text{Diopeter Power(Sphere value)}}$ $r$ = radius of the lens(fixed)

-continued $t$ = thickness of the lens(fixed)

$n_{max}$ = maximum refractive index at optical axis of each lens(fixed)

(e.g., refractive index of the subtrates)

$n(r)$ = refractive index at position $r$, which has a relation, based on lens specs, to voltage ($V$) or current to be applied to the LC to acheive a focal length($f_{GRIN}$)GRIN(gradient index lens) = the design of the LC for adaptive purpose(e.g., based on gradual variation of the refractive index without necessity of curved surfaces, using the birefringence property of liquid crystals In other instances, the lenses 304 may utilize electrowetting techniques for changing an optical power of the lenses 304 based on different levels of voltage or current applied to the lenses 304 from the power source 306. In these instances, the lenses 304 may utilize "liquid-lens" technology, in which the lenses 304 comprise an insulating layer, which may be hydrophobic, and a metal layer (e.g., aluminum). When current or voltage is applied to liquid on that resides within two substrates of the lenses 304, the liquid becomes electrostatically attracted to the metal layer. Thus, the liquid spreads out as it attracts to the metal layer, resulting in the liquid changing shapes. This changing of shapes (based on the amount of applied voltage or current) may alter the optical-power values of the lenses 304. Of course, while liquid-crystal-lens technology and liquid-lens technology has been discussed, it is to be appreciated that the techniques described herein may utilize any other technology in which an optical power of an eyeglass lens changes based on an amount of voltage or current applied to the lenses 304.

The one or more sensors 308, meanwhile, may generate sensor data, which components of eyeglass system 300 may analyze for determine information indicative of where a user is currently looking, which in turn may be used for determining a voltage or current level to apply to the lenses using the power source 306. As described above, the sensors may comprise one or more cameras for generating image data, such as a first camera coupled to a first side of the frame and having a FOV of a left eye of the user and a second camera coupled to a second side of the frame and having a FOV of a right eye of the user. Of course, any number of cameras may be used as long as the resulting image data includes one or more eyes of the user. Further, the cameras may comprise RGB camera(s), infrared (IR) camera(s), and/or the like. In instances where IR camera(s) are used, the sensors may include one or more IR lights directed toward the eye(s) of the user.

In some instances, the sensors 308 may further include one or more temperature sensors configured to determine an ambient temperature. In some instance, the ambient temperature may alter the needed voltage or current for achieving a desired optical-power value. Thus, the temperature determined by the temperature sensor may be used, in part, for determining the voltage or current level to apply to the lenses 304 to achieve a desired optical power. For example, in one example, the eyeglass system may store multiple tables or other data structures that stores voltage/current values to apply to achieve different optical-power values, as described below with reference to datastore 322. In these instances, the current temperature may be used to select the appropriate table for determining the appropriate current or voltage to apply to the lenses.

As illustrated, the eyeglass system 300 further includes one or more processors 310 and memory 312. The processors 310 may include a central processing unit (CPU) for processing data and computer-readable instructions, and the memory 204 may store computer-readable instructions that are executable on the processor(s) 310. The memory 312 may individually include volatile random access memory (RAM), non-volatile read only memory (ROM), non-volatile magnetoresistive (MRAM) and/or other types of memory.

As illustrated, the memory 312 may store an instruction component 314, a degree-of-convergence (DoC) component 316, sensor data 318, prescription data 320, and/or DoC-to-voltage/current data 322. It is to be appreciated that while FIG. 3 illustrates the eyeglass system 300 as storing these components and data, in other instances one or more other devices may store some or all of the components and data. For example, some of the components and/or data may be stored on a mobile device associated with the user that connects to the eyeglass system 300 via one or more networks (e.g., a short-range wireless network, such as Bluetooth), on a server that connects to the eyeglass system via one or more networks (e.g., a wide-area network (WAN), a local area network (LAN), etc.), and/or any other device(s). Thus, it is to be appreciated that the determinations, calculations, and other techniques described herein may be performed at the eyeglass system 300, on a mobile device of the user, at a remote server, and/or at any other devices or across a combination of these devices.

In general, the DoC component 316 may be configured to determine a voltage or current level to apply to the lenses 304, while the instruction component 314 may be configured to generate and send an instruction to the power source 306 to apply the determined voltage or current level to the lenses 304. The sensor data 318, meanwhile, may comprise data generated by the one or more sensors 308, such as image data generated by one or more cameras.

The prescription data 320 may indicate an optical prescription associated with a user of the eyeglass system 300. For example, the user may input the prescription data into a computing device (e.g., mobile phone, laptop, etc.), which may communicate the prescription data 320 to the eyeglass system 300. For example, the user may capture an image of a prescription and upload the image to an application stored on a mobile device, which may perform image and character recognition to identify the prescription data 320. In another example, the user may use an application to manually (e.g., using a keyboard, audibly, etc.) input the prescription data 320 into the application. After the application receives the prescription data 320, the device may then send this prescription data 320 to the eyeglass system 300.

Figure 4:
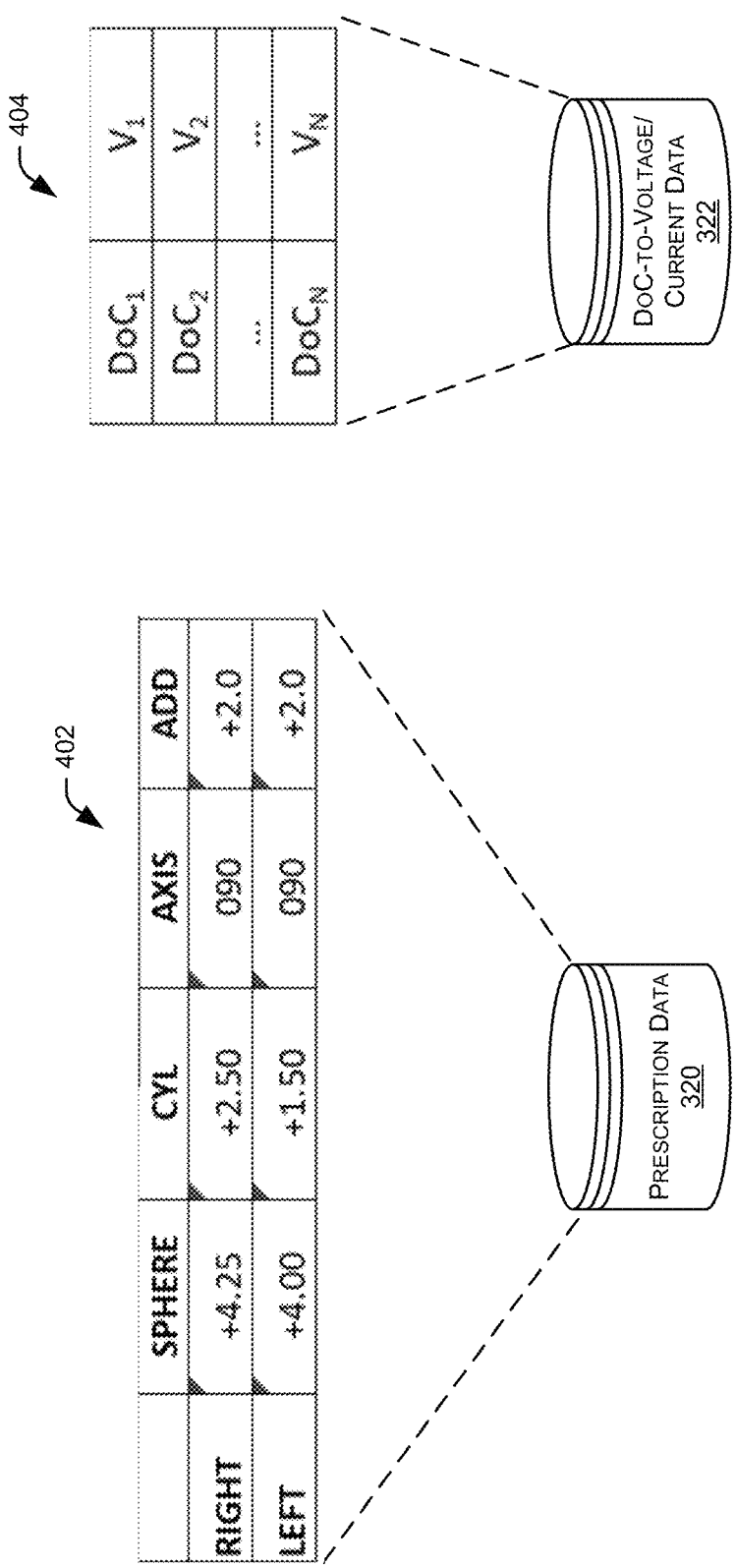
FIG. 4 illustrates example prescription data, associated with a user of the eyeglass system, that the eyeglass system may store. This figure also illustrates example degree-of-convergence-(DoC)-to-voltage/current data that the eyeglass system may store. The eyeglass system may use the DoC-to-voltage/current data for determining a voltage or current level to apply to lenses of the eyeglass system for achieving a desired optical-power value.

FIG. 4, for example, illustrates an example prescription 402 that may be stored as prescription data 320. As illustrated, the prescription may indicate different prescription values for a right eye of the user and a left eye of the user. The values under "Sphere" may indicate whether the prescription is for farsighted-ness or nearsighted-ness, with a plus ("+") indicating the former and a negative ("−") indicating the latter. In this example, the prescription 402 indicates that prescription 402 is for farsighted-ness, with a value of 4.25 for the right eye and 4.00 for the left eye. The "CYL", meanwhile, describes any sort of astigmatism, if any. The "AXIS" indicates which way the astigmatism is oriented. In this example, the right eye has an astigmatism of +2.50 and an axis of 090 in the right eye and +1.50 and 090 in the left eye. In this example, the prescription 402 includes an additive value ("ADD") used for bifocals. In this example, a value of 2.00 is added to each of the SPHERE values for each of the left eye and the right eye when the user is looking at near-range objects. Of course, while FIG. 4 illustrates an example prescription 402, in other instances the prescription data 302 may store trifocal prescriptions and/or the like.

The DoC-to-voltage/current data 322, meanwhile, may store an association between different DoC values and respective voltage and/or current levels. As described above, and in additional detail below, the DoC values may comprise ratio values that are indicative of a distance between a user's eyes and an object at which the user is looking. FIG. 4, for instance, illustrates that a first DoC value ($DoC_1$) may be associated with a first voltage or current value ($V_1$), a second DoC value ($DoC_2$) may be associated with a second voltage or current value ($V_2$), and so forth. It is to be appreciated that each voltage or current value may be associated with a desired optical-power value for the respective DoC value. Further, while FIGS. 3 and 4 describe DoC values, it is to be appreciated that the datastore 322 may store an association between voltage or current levels and any other characteristic of the current distance between the user's eyes the object at which they are looking.

Returning to FIG. 3, the DoC component 316 may determine a current DoC value, which may be used to determine, via the datastore 322, the appropriate voltage or current level to apply to the lenses for achieving the desired optical-power value. As illustrated, the DoC component 316 may include an eye-identification component 324, a pupil-identification component 326, a measurement component 328, and a calculation component 330.

To begin, the eye-identification component 324 may analyze the sensor data 318, such as image data to identify the left eye of the user and the right eye of the user in the image data. In some instances, the eye-identification component 324 may use one or more computer-vision techniques to identify the location of the eyes. For example, the eye-identification component 324 may analyze the image data using a machine-learned model to identify a portion of the image data that depicts the left eye of the user and a portion of the image data that depicts the right eye of the user. In some instances, this machine-learned model identifies the respective eyes based on landmarks around each eye, the shape of the eye, the color of the eye relative to the surrounding skin, and/or the like.

Upon the eye-identification component 324 identifying each eye, the pupil-identification component 326 may also use the respective image data to identify a pupil of the left eye and a pupil of the right eye. For example, the pupil-identification component 326 may generate, from the image data, a grayscale version of the image data. Thereafter, the pupil-identification component 326 may perform gradient threshold to identify which part of the grayscale image data is darker than a predefined value, such as 128, where zero (0) represents black and 256 represents white. Stated otherwise, given that the pupil is the darkest portion of the human eye, the gradient-thresholding techniques may identify the darkest part of the eye, which corresponds to the pupil. In some instances, the eyeglass system may perform auto-calibration techniques for determining this threshold value, with the threshold value being based at least in part on current lighting conditions. Of course, while the above example describes one technique for identifying the location of the pupils, other techniques may also be used.

After the pupil-identification component 326 identifies the locations of each eye and the locations of respective pupils within the image data, the measurement component 328 may perform one or more measurements for determining a DoC or convergence angle between the user's eyes, which in turn may be used to determine a voltage or current level to apply to the lenses (for causing the lenses to exhibit a desired optical-power value). In one example, the measurement component 328 determines a first distance between a first edge (e.g., a left edge) of the left eye and a center of a pupil of the left eye, as well as a second distance between the first edge of the left eye and a second edge (e.g., a right edge) of the left eye. In addition, the measurement component 328 may determine a third distance between the first edge (e.g., the left edge) of the right eye and a center of a pupil of the right eye, as well as a fourth distance between the first edge of the right eye and the second edge (e.g., the right edge) of the right eye.

After determining these distances, the calculation component 330 may calculate a first ratio comprising a ratio between the first distance and the second distance. In addition, the calculation component 330 may calculate a second ratio comprising a ratio between the third distance and the fourth distance. Finally, the calculation component 330 may calculate a third ratio comprising a ratio between the first ratio and the second ratio. As will be appreciated, when a user is looking at a distant object, the optical axes of the eyes of the user are generally parallel. Thus, the third ratio (DoC value) may be approximately one (e.g., between 0.9 and 1.1 or between 0.95 and 1.05). When, however, the user is looking at a near object, and thus the optical axes are directed somewhat towards each other, the third ratio (DoC value) may be greater than one.

Therefore, the calculation component 330 may be configured to map this third ratio, representing the DoC of the eyes of the user, to a voltage or current level that will result in the appropriate optical-power value and may store this association in the datastore 322 along with other DoC-to-voltage/current-level associations. For example, if a particular value of the third ratio (e.g., approximately one, 1.0 to 1.1, etc.) indicates that the user is looking at a distant object, then the eyeglass system or the other device may be configured to apply a voltage or current level that results in an optical-power value of the lens specified in the prescription data of the user for viewing distant objects. If, however, the value of the third ratio (e.g., greater than 1.1) indicates that the user is looking at a mid-range or near object, then the eyeglass system or the other device may be configured to apply a voltage or current level that results in an optical-power value of the lens specified in the prescription data for the user for viewing mid-range or near objects. Of course, while this example describes two optical-power values for the example of bifocals, in other instances a greater number of optical-power values (and, thus, voltage or current levels) may applied. For example, in the trifocal example, the eyeglass system or the other device may be configured to apply a first optical-power value for a DoC of 1.0 to 1.1, a second optical-power value for a DoC of 1.1 to 1.3, and a third optical-power value for a DoC of greater than 1.3 Further, while the above example describes example DoC values, it is to be appreciated that other measurements, ratios, thresholds, and the like the may be utilized for determining the appropriate voltage or current level to apply to the lenses at any given time. In either instance, the calculation component 330 may, in some instances, use the prescription data and the equation described above to determine the voltage or current levels to apply to lenses of the eyeglass system 300 to achieve the different optical-power values specified in the prescription data 320.

Figure 5:
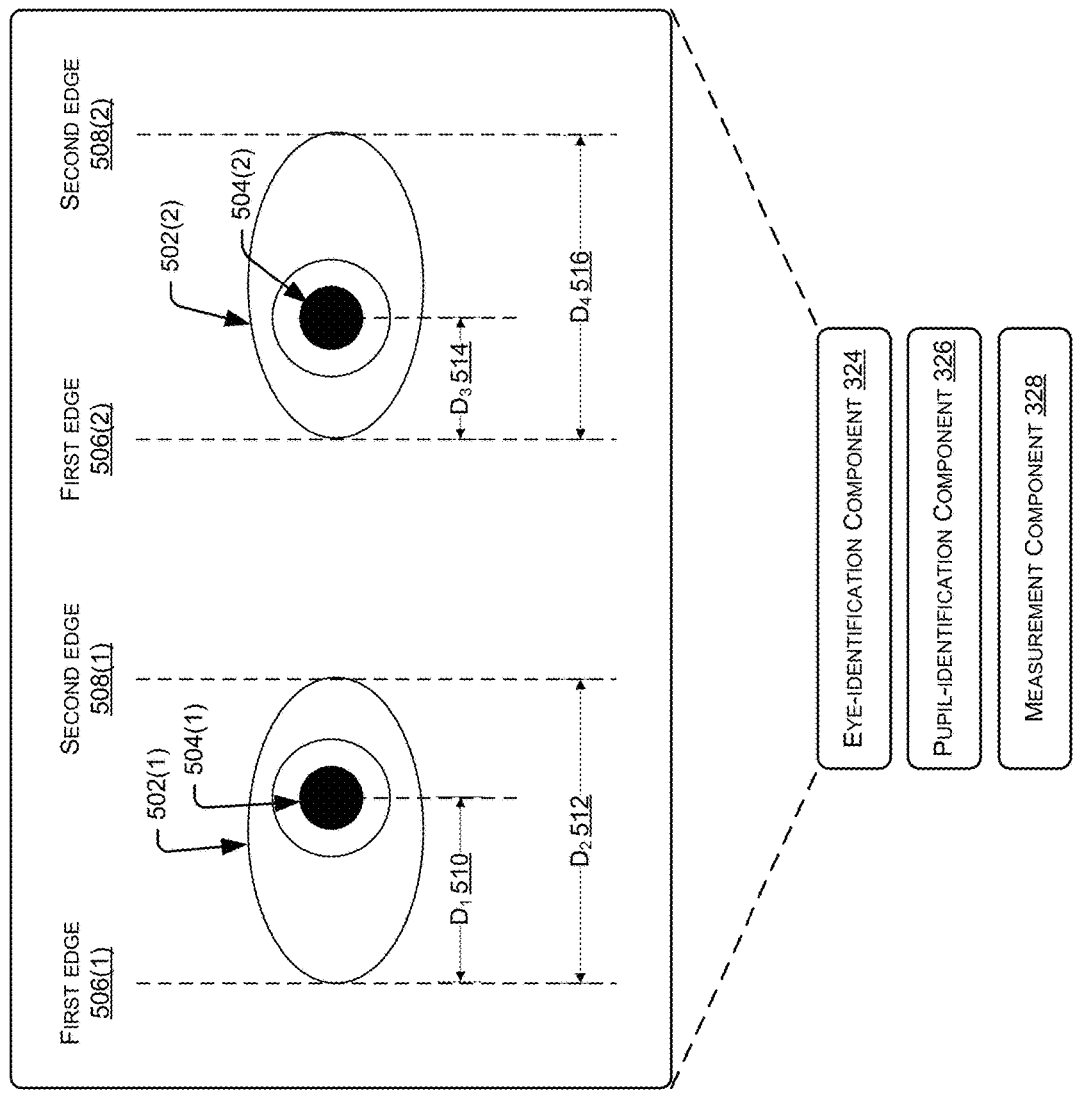
FIG. 5 illustrates example components of the eyeglass system for identifying, from sensor data, eyes and pupils of a user wearing the eyeglass system and measuring certain distances associated with the eyes and pupils.

FIG. 5 illustrates example components of the eyeglass system 300 for identifying, from the sensor data 318, eyes and pupils of a user wearing the eyeglass system and measuring certain distances associated with the eyes and pupils. As noted above, the eye-identification component 324 may analyze the sensor data to identify a right eye 502(1) of the user and a left eye 502(2) of the user. The pupil-identification component 326 may also use the sensor data to identify a right pupil 504(1) and a left pupil 504(2).

After identifying the eyes and the pupils, the measurement component 328 may determine a first distance 510 between a first edge 506(1) of the right eye 502(1) and a center of the right pupil 504(1), as well as a second distance 512 between the first edge 506(1) of the right eye 502(1) and a second edge 508(1) of the right eye 502(1). In addition, the measurement component 328 may determine a third distance 514 between a first edge 506(2) of the left eye 502(2) and a center of the left pupil 504(2), as well as a fourth distance 516 between the first edge 506(2) of the left eye 502(2) and a second edge 508(2) of the left eye 502(2). As described immediately below, these distance may be used to determine a current DoC value by the calculation component 330, which in turn may be used to determine a voltage or current value to apply to achieve a desired optical-power value of the lenses 304.

FIG. 6 illustrates example operation of the calculation component 330, which may use the measurements determined by the measurement components 328 for determining a DoC of the eyes of the user for determining a desired voltage or current value and/or optical-power value. As illustrated, the calculation component 330 may first compute a first ratio between the first distance 510 and the second distance 512. In addition, the calculation component 330 may compute a second ratio between the third distance 514 and the fourth distance 516. Thereafter, the calculation component 330 may compute a third ratio between the first and second ratios. In this example where the eyeglass system 300 operates as trifocals, the calculation component 330 may also store an indication of example DoC ranges associated with example optical-power values. For example, FIG. 6 indicates that if the third ratio (DoC value) is between 1.0 and 1.1, then a first optical-power value is to be applied to the lenses, if the third ratio is between 1.1 and 1.3, then a second optical-power value is to be applied to the lenses, and if third ratio is greater than 1.3, then a third optical-power value is to be applied to the lenses. Of course, while a few example threshold values are described, it is to be appreciated that any other threshold value(s) may be used, which may be based on factors such as camera configuration and the like.

Figure 7B:
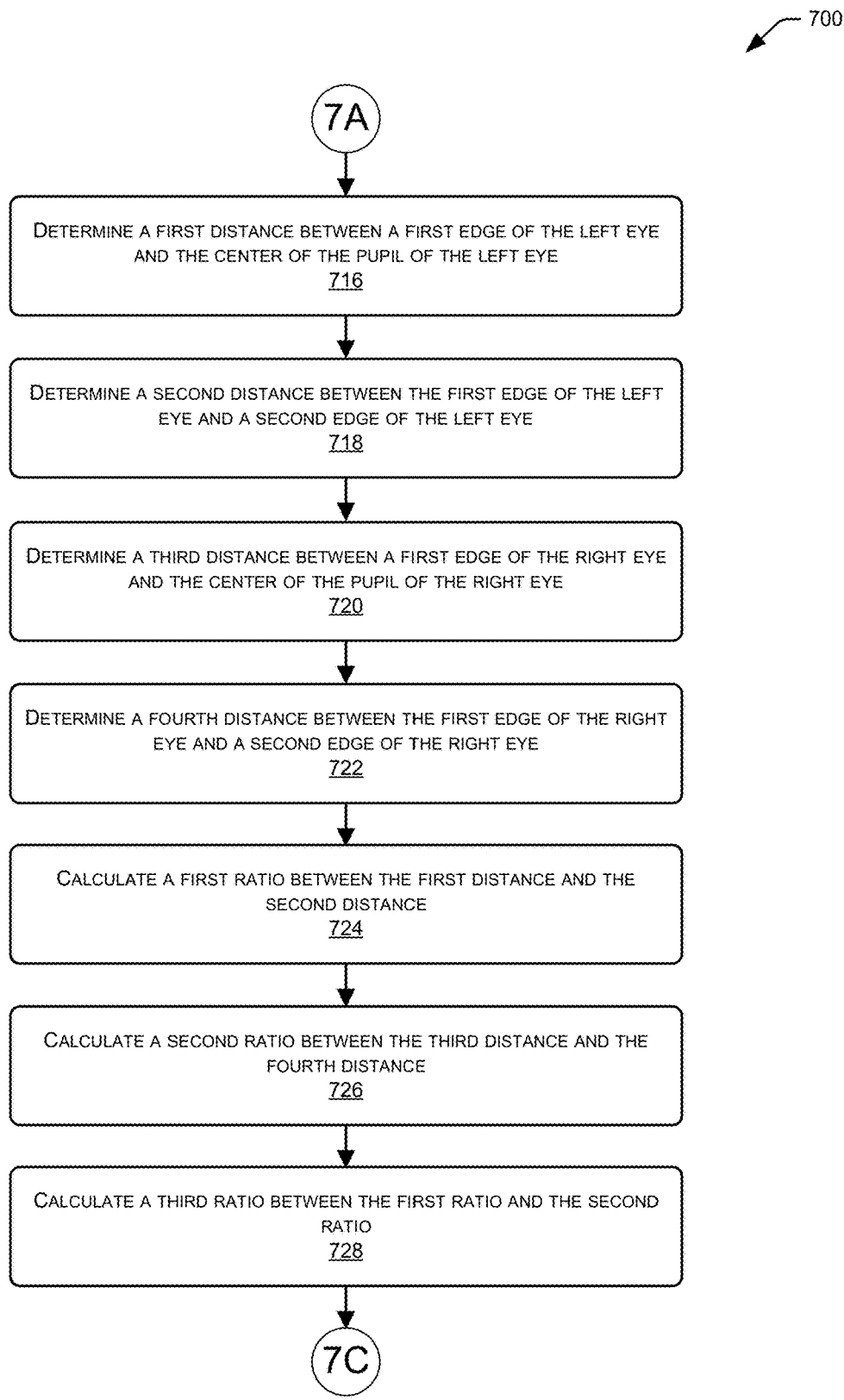
Figure 7C:
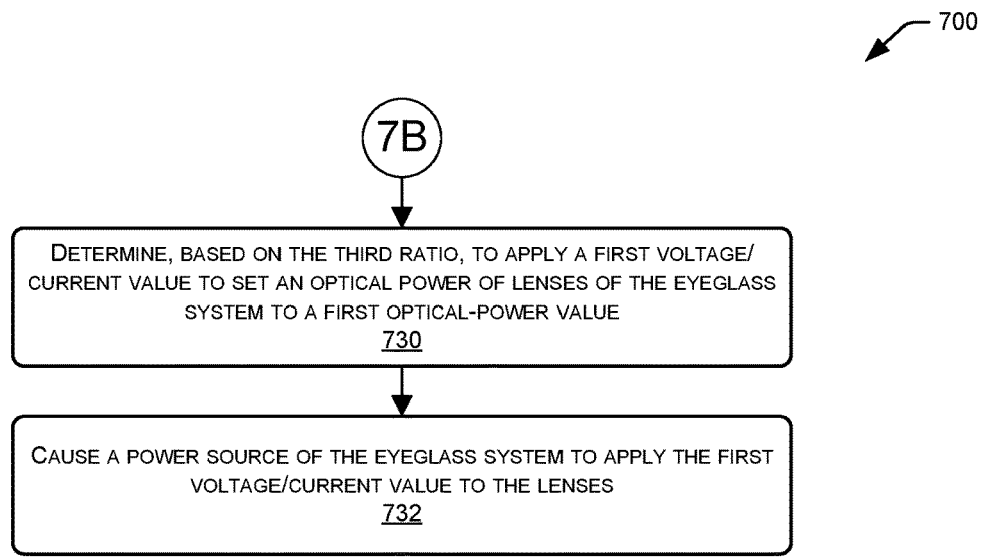

FIGS. 7A-C collectively illustrate a flow diagram of an example process 700 for automatically changing an optical power of lenses of an eyeglass system based on a current DoC of the eyes of a user wearing the eyeglass system. The process 700, as well as each process described herein, may be implemented in hardware, software, or a combination thereof. In the context of software, the described operations represent computer-executable instructions stored on one or more computer-readable storage media that, when executed by one or more hardware processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation. Finally, while operations of the processes described herein are described as being performed by the eyeglass system 300, in other instances the operations may additionally or alternatively be performed by and/or across one or more other devices.

At an operation 702, the eyeglass system 300 may store prescription data associated with a user of the eyeglass system 300. For example, a user may capture an image of a prescription associated with the user using a mobile phone or other electronic device that includes a camera. An application on the mobile device or other device may then perform image recognition on the image data for identifying the prescription data indicated in the prescription. This information may be stored on the eyeglass system. In another example, a user may manually input the prescription data using a user interface (UI) of a device, which may then be provided to the eyeglass system. Of course, while a few examples are provided, it is to be appreciated that the prescription data may be provided to the eyeglass system in any other manner.

At an operation 704, the eyeglass system 300 may calculate respective voltage or current values to achieve respective optical-power values. For example, the eyeglass system 300 may be calibrated by applying different voltage or current values and determining the resulting optical-power values. In some instances, these calculations may be performed "offline" and prior to the eyeglass system 300 being provided to a user.

At an operation 706, the eyeglass system 300 may store an association between the respective voltage or current values and the respective optical-power values. For example, the eyeglass system may store one or more tables or other data structures indicating these associations. As introduced above, in some instances the eyeglass system 300 stores multiple tables, each of which may be associated with a respective temperature range, given that temperature can affect the optical-power value of the lenses.

At an operation 708, the eyeglass system 300 may analyze image data generated by one or more cameras of the eyeglass system 300 to identify a left eye of the user wearing the eyeglasses. For example, the eyeglass system 300 may use computer-vision techniques to analyze the image data to identify the location of the left eye within the image data. This may include, for example, identifying a perimeter of the left eye of the user wearing the eyeglass system 300.

At an operation 710, the eyeglass system 300 may analyze image data generated by one or more cameras of the eyeglass system 300 to identify a right eye of the user wearing the eyeglasses. Again, the eyeglass system 300 may use computer-vision techniques to analyze the image data to identify the location of the right eye within the image data. This may include, for example, identifying a perimeter of the left eye of the user wearing the eyeglass system 300.

At an operation 712, the eyeglass system 300 may determine, from the sensor data, a center of a pupil of the left eye of the user. In some instances, this may include performing binary gradient thresholding, as described above, to classify each pixel as either white or black. Given that the pupil is the darkest portion of the eye, the pixels that are labeled as black and form a circular shape may be deemed the pupil in some instances.

At an operation 714, the eyeglass system 300 may determine, from the sensor data, a center of a pupil of the right eye of the user. Again, this may include performing binary gradient thresholding, as described above, to classify each pixel as either white or black. Given that the pupil is the darkest portion of the eye, the pixels that are labeled as black and form a circular shape may be deemed the pupil in some instances.

FIG. 7B continues the illustration of the process 700 and includes, at an operation 716, the eyeglass system determining a first distance between a first edge of the left eye and the center of the pupil of the left eye. As described above, with reference to FIG. 5, the measurement component 328 may analyze the labeled image data to determine this measurement. At an operation 718, the eyeglass system 300 determines a second distance between the first edge of the left eye and a second edge of the left eye, which again may be performed by the measurement component 328.

At an operation 720, the eyeglass system 300 determines a third distance between the first edge of the right eye and the center of the pupil of the right eye. At an operation 722, the eyeglass system 300 determines a fourth distance between the first edge of the right eye and the second edge of the right eye.

At an operation 724, the eyeglass system 300 calculates a first ratio between the first distance and the second distance. An example of this calculation is described above with reference to the calculation component 330 of FIG. 6. At an operation 726, the eyeglass system 300 calculates a second ratio between the third distance and the fourth distance. Again, the calculation component 330 may calculate this ratio. At an operation 728, the eyeglass system 300 calculates a third ratio between first ratio and the second ratio, which may be performed by the calculation component 330 in some instances.

FIG. 7C concludes the illustration of the process 700 and includes, at an operation 730, the eyeglass system 300 determining, based at least in part on the third ratio, to apply the first voltage or current value to set the optical power of first and second lenses at the first value. In some instances, this may comprise accessing the DoC-to-Voltage/Current datastore 322 to determine the voltage or current value to apply based on the third ratio (or DoC value). In other instances, this may include accessing data storing associations between DoC values, in this example the third ratio, and respective target optical powers. That is, while the operation 730 describes determining a voltage or current value based on the third ratio, in some instances the process 700 may first determine a target optical power, which in turn may be used to determine a voltage or current value. In these examples, the eyeglass system may store data associating DoC values to target optical powers, and target optical powers to voltage or current values.

At an operation 732, the eyeglass system 300 cause a power source to apply the first voltage or current value to first and second lenses of the eyeglass system. For example, the instruction component 314 may send an instruction to the power source to apply the determined voltage or current value.

Figure 8:
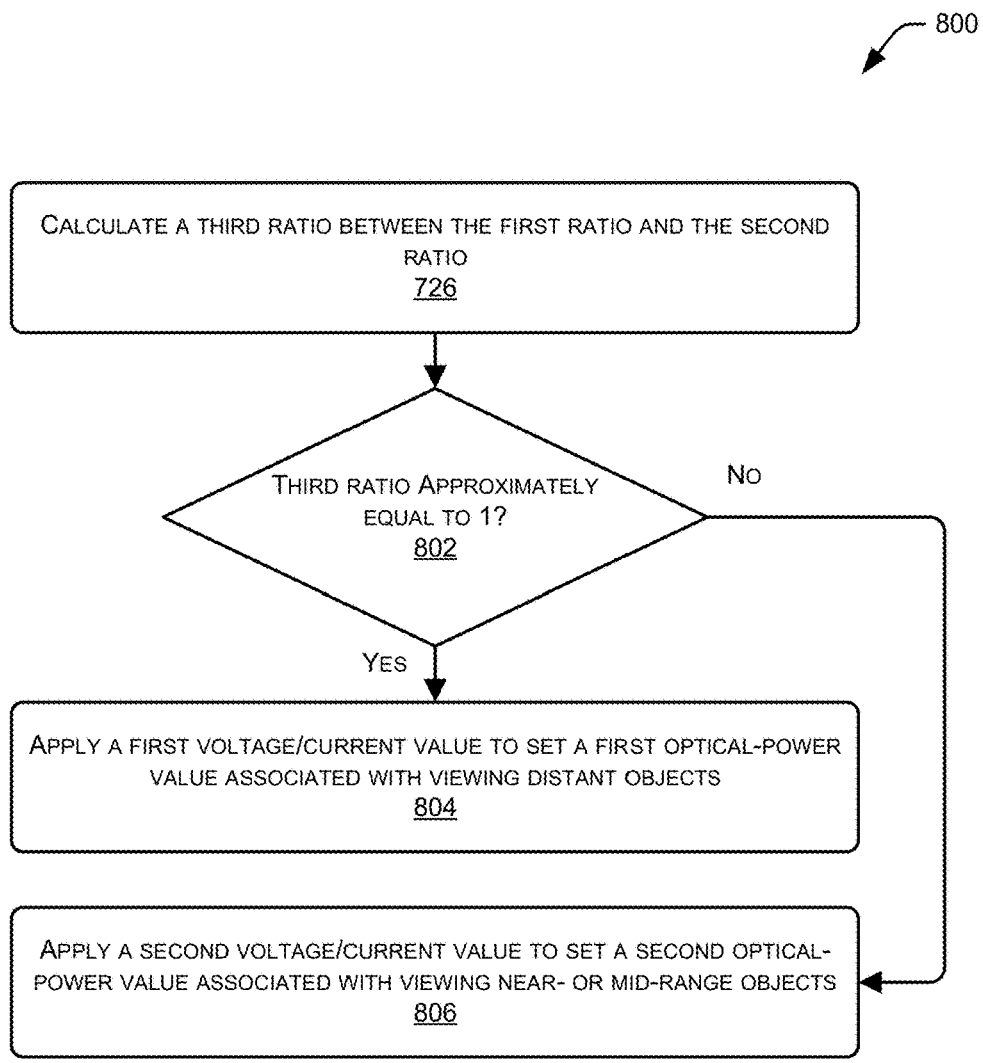
FIG. 8 illustrates a flow diagram of an example process in which an eyeglass system described herein operates as bifocals by determining whether to cause lenses to operate at a first optical-power value or a second optical-power value.

FIG. 8 illustrates a flow diagram of an example process 800 in which an eyeglass system described herein operates as bifocals by determining whether to cause lenses to operate at a first optical-power value or a second optical-power value. An operation 726 is described above and includes the eyeglass system 300 calculating a third ratio between the first and second ratios described above. For example, to calculate the third ratio, the eyeglass system 300 may initially analyze image data generated by one or more cameras of the eyeglass system 300 to identify a left eye of the user wearing the eyeglasses. For example, the eyeglass system 300 may use computer-vision techniques to analyze the image data to identify the location of the left eye within the image data. This may include, for example, identifying a perimeter of the left eye of the user wearing the eyeglass system 300. The eyeglass system 300 may then analyze image data generated by one or more cameras of the eyeglass system 300 to identify a right eye of the user wearing the eyeglasses. Again, the eyeglass system 300 may use computer-vision techniques to analyze the image data to identify the location of the right eye within the image data. This may include, for example, identifying a perimeter of the left eye of the user wearing the eyeglass system 300.

Thereafter, the eyeglass system 300 may determine, from the sensor data, a center of a pupil of the left eye of the user. In some instances, this may include performing binary gradient thresholding, as described above, to classify each pixel as either white or black. Given that the pupil is the darkest portion of the eye, the pixels that are labeled as black and form a circular shape may be deemed the pupil in some instances. Next, the eyeglass system 300 may determine, from the sensor data, a center of a pupil of the right eye of the user. Again, this may include performing binary gradient thresholding, as described above, to classify each pixel as either white or black. Given that the pupil is the darkest portion of the eye, the pixels that are labeled as black and form a circular shape may be deemed the pupil in some instances.

Next, the eyeglass system determining a first distance between a first edge of the left eye and the center of the pupil of the left eye. As described above, with reference to FIG. 5, the measurement component 328 may analyze the labeled image data to determine this measurement. In addition, the eyeglass system 300 determines a second distance between the first edge of the left eye and a second edge of the left eye, which again may be performed by the measurement component 328. The eyeglass system 300 may then determine a third distance between the first edge of the right eye and the center of the pupil of the right eye and a fourth distance between the first edge of the right eye and the second edge of the right eye. In addition, the eyeglass system 300 calculates a first ratio between the first distance and the second distance and a second ratio between the third distance and the fourth distance. Again, the calculation component 330 may calculate this ratio. The operation 726 may then comprise calculating a ratio of the first and second ratios.

An operation 802 represents determining whether the third ratio is approximately equal to one (e.g., between 0.9 and 1.1 or between 0.95 and 1.05). If so, then an operation 804 represents applying a first voltage or current value to the first and second lenses to set an optical power of the lenses to a first optical-power value associated with viewing distant objects.

If the third ratio is not approximately equal to one (e.g., between 0.9 and 1.1 or between 0.95 and 1.05), then an operation 806 represents applying a second voltage or current value to the first and second lenses to set the optical power of the lenses to a second optical-power value associated with viewing near- or mid-range objects. That is, if the third ratio is greater than one by a threshold amount (e.g., 0.05, 0.1, 0.2 etc.), then the process 800 may perform the operation 806.

Figure 9:
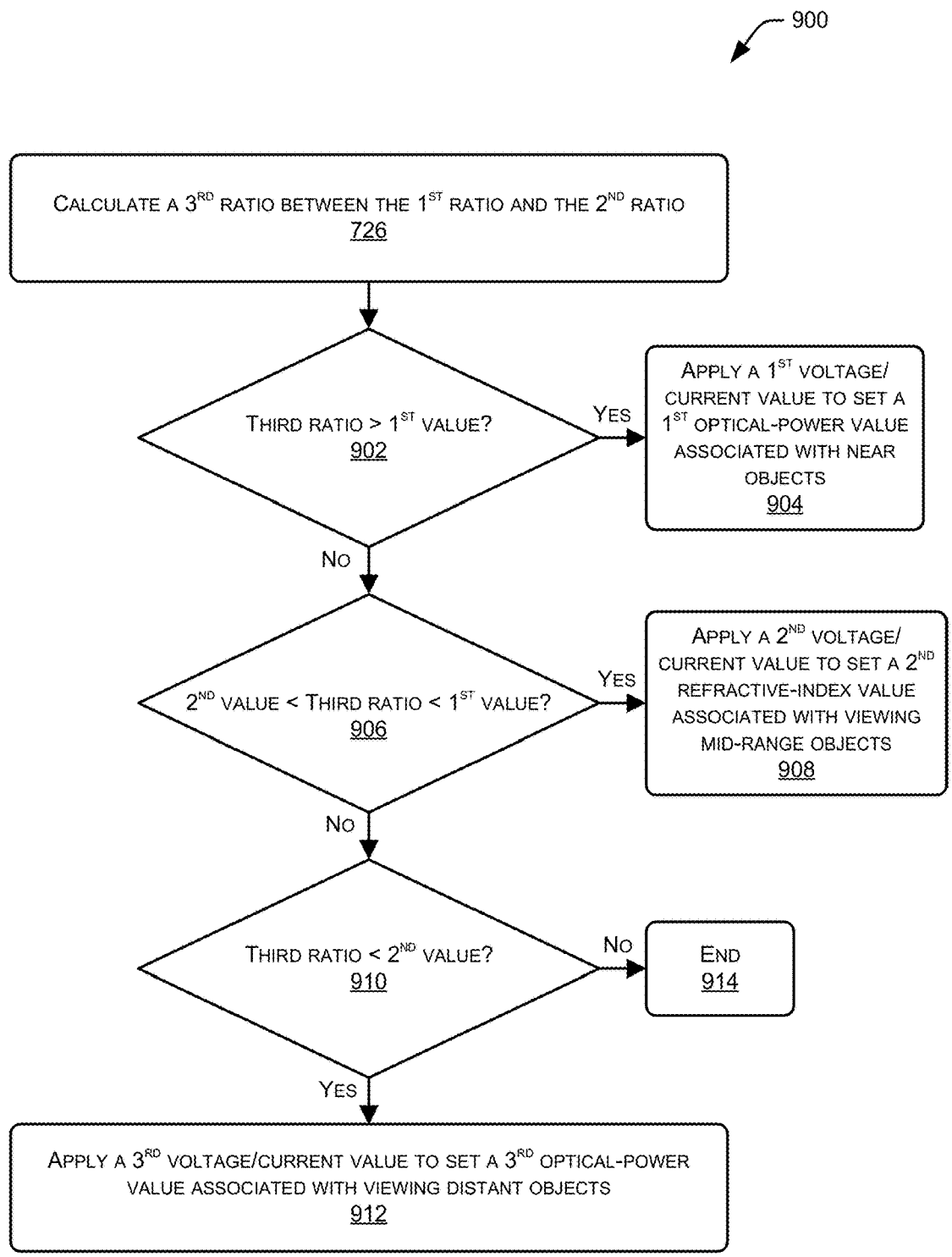
FIG. 9 illustrates a flow diagram of an example process in which an eyeglass system described herein operates as trifocals by determining whether to cause lenses to operate at a first optical-power value, a second optical-power value, or a third optical-power value.

FIG. 9 illustrates a flow diagram of an example process 900 in which an eyeglass system described herein operates as trifocals by determining whether to cause lenses to operate at a first optical-power value, a second optical-power value, or a third optical-power value. An operation 726 is described above and includes the eyeglass system 300 calculating a third ratio between the first and second ratios described above. Again, to calculate the third ratio, the eyeglass system 300 may initially analyze image data generated by one or more cameras of the eyeglass system 300 to identify a left eye of the user wearing the eyeglasses. For example, the eyeglass system 300 may use computer-vision techniques to analyze the image data to identify the location of the left eye within the image data. This may include, for example, identifying a perimeter of the left eye of the user wearing the eyeglass system 300. The eyeglass system 300 may then analyze image data generated by one or more cameras of the eyeglass system 300 to identify a right eye of the user wearing the eyeglasses. Again, the eyeglass system 300 may use computer-vision techniques to analyze the image data to identify the location of the right eye within the image data. This may include, for example, identifying a perimeter of the left eye of the user wearing the eyeglass system 300.

Thereafter, the eyeglass system 300 may determine, from the sensor data, a center of a pupil of the left eye of the user. In some instances, this may include performing binary gradient thresholding, as described above, to classify each pixel as either white or black. Given that the pupil is the darkest portion of the eye, the pixels that are labeled as black and form a circular shape may be deemed the pupil in some instances. Next, the eyeglass system 300 may determine, from the sensor data, a center of a pupil of the right eye of the user. Again, this may include performing binary gradient thresholding, as described above, to classify each pixel as either white or black. Given that the pupil is the darkest portion of the eye, the pixels that are labeled as black and form a circular shape may be deemed the pupil in some instances.

Next, the eyeglass system determining a first distance between a first edge of the left eye and the center of the pupil of the left eye. As described above, with reference to FIG. 5, the measurement component 328 may analyze the labeled image data to determine this measurement. In addition, the eyeglass system 300 determines a second distance between the first edge of the left eye and a second edge of the left eye, which again may be performed by the measurement component 328. The eyeglass system 300 may then determine a third distance between the first edge of the right eye and the center of the pupil of the right eye and a fourth distance between the first edge of the right eye and the second edge of the right eye. In addition, the eyeglass system 300 calculates a first ratio between the first distance and the second distance and a second ratio between the third distance and the fourth distance. Again, the calculation component 330 may calculate this ratio. The operation 726 may then comprise calculating a ratio of the first and second ratios.

An operation 902 represents determining whether the third ratio is greater than or equal to a first threshold value. Each threshold value described in the process 900 may be based, at least in part, on factors such as a location of the sensors (e.g., cameras) on the eyeglass system and the like. If the result of the operation 902 is yes, then an operation 904 represents applying a first voltage or current value to the first and second lenses to set an optical power of the lenses to a first optical-power value associated with viewing near objects. If the third ratio is not approximately greater than or equal to the first threshold value, then an operation 906 represents determining whether the third ratio is between the first threshold value and a second threshold value. If so, then an operation 908 represents applying a second voltage or current value to the first and second lenses to set the optical power of the lenses to a second optical-power value associated with viewing mid-range objects.

If the third ratio is not within that range, then an operation 910 represents determining whether the third ratio is less than the second threshold value. If so, then an operation 912 represents applying a third voltage or current value to the first and second lenses to set the optical power of the lenses to a third optical-power value associated with viewing distant objects. If not, then the process 900 may end at an operation 914.

Figure 10:
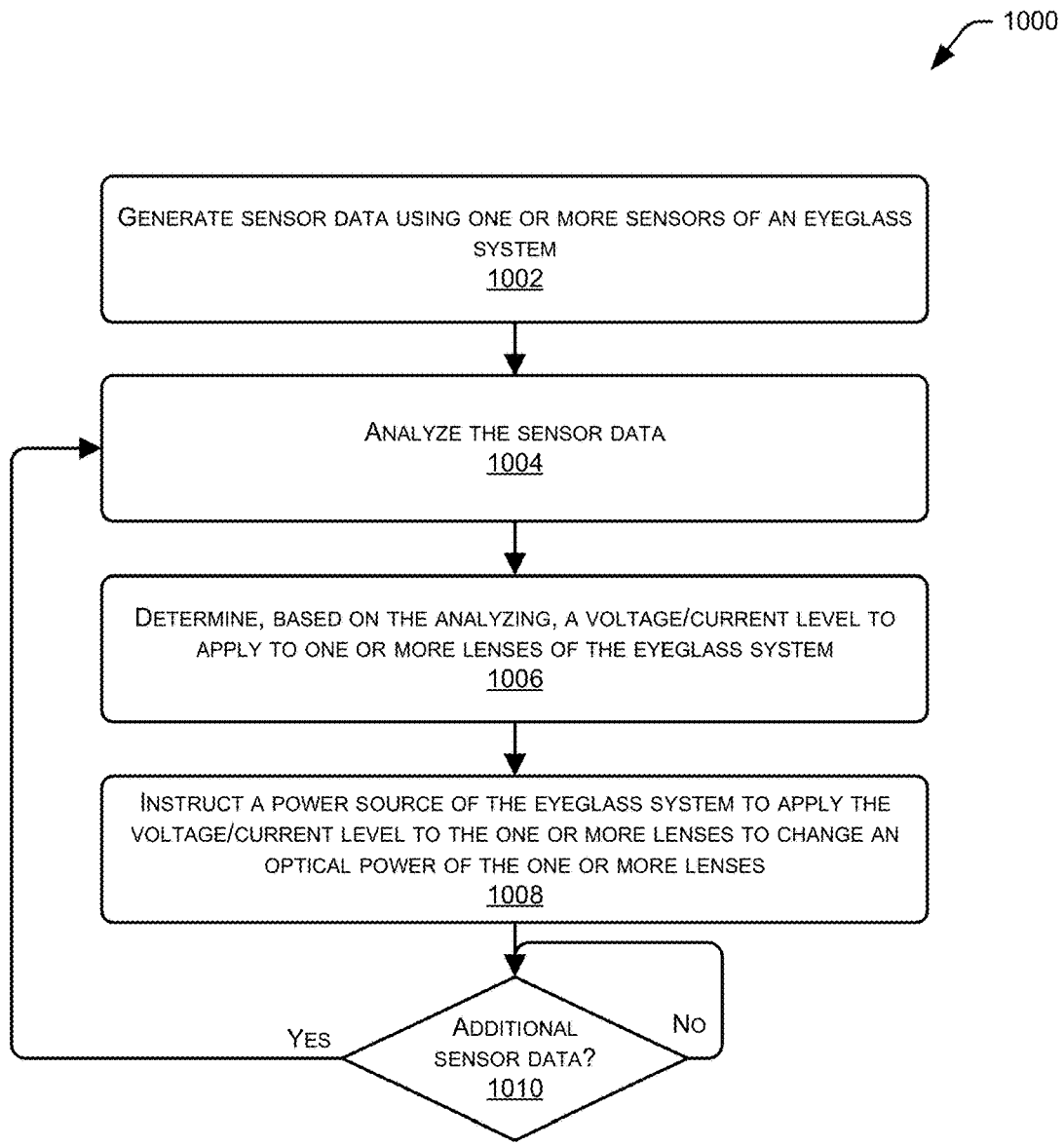
FIG. 10 illustrates a flow diagram of an example process for determining a voltage or current level to apply to lenses of an eyeglass system based on analyzing sensor data generated by one or more sensors of the eyeglass system.

FIG. 10 illustrates a flow diagram of an example process 1000 for determining a voltage or current value to apply to lenses of an eyeglass system based on analyzing sensor data generated by one or more sensors of the eyeglass system.

At an operation 1002, the eyeglass system 300 may generate sensor data using one or more sensors. As described above, this may include one or more cameras generating image data representing one or both eyes of a user wearing the eyeglass system.

At an operation 1004, the eyeglass system 300 may analyze the sensor data. This may include identifying the eyes in the image data using computer-vision techniques and identifying the pupils in the image data using binary gradient thresholding. In addition, this operation may include measuring one or more distances between portions of the eyes and calculating one or more ratios, as described above.

At an operation 1006, the eyeglass system 300 may determine, based on the analyzing, a voltage or current value to apply to the lens. For example, the eyeglass system may use the DoC (e.g., the third ratio described above) to determine voltage or current value to apply. For example, the eyeglass system may access the DoC-to-Voltage/Current data 322 to determine, based on the DoC value, the appropriate voltage or current value to apply. As described above, in some instances this operation may comprise first determining, based on the analyzing performed at the operation 1004, the target focal power, which in turn may be used to determine the voltage or current level.

At an operation 1008, the eyeglass system 300 may cause the power source to apply the voltage or current value to the lens to change an optical power of the lens. For example, the instruction component 314 may send an instruction to the power source 306 to apply the voltage or current value to the lens(es).

An operation 1010 represents determining whether additional sensor data has been generated. That is, this operation 1010 represents determining whether new image data has been generated, which may indicate that the user is looking at a different object, which may necessitate a change in optical power of the lens(es). If not, the process 1000 may loop back to this operation. If so, however, then the process 1000 may loop back to the operation 1004 for analyzing the additional sensor data for, potentially, applying a different voltage or current value for changing the optical power of the lens(es).

In some implementations, the processors(s) 310 may include a central processing unit (CPU), a graphics processing unit (GPU), both CPU and GPU, a microprocessor, a digital signal processor and/or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processors(s) 310 may possess its own local memory, which also may store program modules, program data, and/or one or more operating systems. The processors(s) 310 may be located in a single device or system, or across disparate devices or systems, which may be owned or operated by various entities.

The memory 312 may include volatile and nonvolatile memory, removable and non-removable media implemented in any method or technology for storage of information, such as computer-readable instructions, data structures, program modules, or other data. Such memory includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 312 may be implemented as computer-readable storage media ("CRSM"), which may be any available physical media accessible by the processor(s) 312 to execute instructions stored on the memory 312. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processors(s) 312.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. An eyeglass system comprising:
a frame;
a first lens coupled to the frame;
a second lens coupled to the frame;
a power source configured to provide at least: (1) a first voltage or first current to the first and second lenses to set an optical power of the first and second lenses to a first value, and (2) a second voltage or second current to the first and second lenses to set the optical power at a second value;
a first camera coupled to the frame to generate first image data of a left eye of a user wearing the eyeglass system;
a second camera coupled to the frame to generate second image data of a right eye of the user;
one or more processors; and
one or more computer-readable media storing computer-executable instructions that, when executed, cause the one or more processors to perform acts comprising:
identifying a representation of the left eye in the first image data;
identifying a representation of the right eye in the second image data;
determining, based at least in part on the first image data, a center of a pupil of the left eye;
determining, based at least in part on the second image data, a center of a pupil of the right eye;
determining a first distance between a first edge of the left eye and the center of the pupil of the left eye;
determining a second distance between the first edge of the left eye and a second edge of the left eye;
determining a third distance between the first edge of the right eye and the center of the pupil of the right eye;
determining a fourth distance between the first edge of the right eye and the second edge of the right eye;
calculating a first ratio between the first distance and the second distance;
calculating a second ratio between the third distance and the fourth distance;
calculating a third ratio between first ratio and the second ratio; and
providing, based at least in part on the third ratio, the first voltage or first current value to the first and second lenses.

2. The eyeglass system as recited in claim 1, wherein:
the providing the first voltage or first current value comprises providing the first voltage or first current value based at least in part on the third ratio being approximately equal to one; and
the one or more computer-readable media further store computer-executable instructions that, when executed, cause the one or more processors to perform an act comprising providing the second voltage or the second current value based at least in part on the third ratio being greater than one.

3. An eyeglass system comprising:
a frame;
a first lens coupled to the frame;
one or more sensors;
a power source;
one or more processors; and
one or more computer-readable media storing computer-executable instructions that, when executed, cause the one or more processors to perform acts comprising:
receiving, from the one or more sensors, sensor data including image data representing a pupil and an edge of at least one eye of a user wearing the eyeglass system;
determining, based at least in part on the sensor data, a distance between the pupil and the edge of the at least one eye;
determining, based at least in part on the distance between the pupil and the edge of the at least one eye, a target optical power for the lens;
determining, based at least in part on the target optical power, a voltage or current value; and
causing the power source to provide the voltage or current value to the first lens.

4. The eyeglass system as recited in claim 3, wherein the one or more sensors comprise a camera to generate the image data.

5. The eyeglass system as recited in claim 3, wherein the at least one eye is a first eye, the pupil is a first pupil, the edge is a first edge, and the distance is a first distance, and wherein the one or more computer-readable media further store computer-executable instructions that, when executed, cause the one or more processors to perform acts comprising:

determining, using the sensor data, the first distance between the first edge of the first eye and a center of the first pupil;

determining, using the sensor data, a second distance between the first edge of the first eye and a second opposing edge of the first eye; and wherein the determining the voltage or current value comprises determining the voltage or current value based at least in part on the first distance and the second distance.

6. The eyeglass system as recited in claim 5, further comprising a second lens, and wherein the one or more computer-readable media further store computer-executable instructions that, when executed, cause the one or more processors to perform acts comprising:

determining, using the sensor data, a second pupil of a second eye of the user;

determining, using the sensor data, a third distance between the first edge of the second eye and a center of the second pupil;

determining, using the sensor data, a fourth distance between the first edge of the second eye and the second opposing edge of the second eye;

and wherein the determining the voltage or current value further comprises determining the voltage or current value based at least in part on the third distance and the fourth distance.

7. The eyeglass system as recited in claim 6, wherein the one or more computer-readable media further store computer-executable instructions that, when executed, cause the one or more processors to perform acts comprising:

calculating a first ratio between the first distance and the second distance;

calculating a second ratio between the third distance and the fourth distance;

calculating a third ratio between the first ratio and the second ratio;

and wherein the determining the voltage or current value is further based at least in part on the third ratio.

8. The eyeglass system as recited in claim 7, wherein the one or more computer-readable media further store computer-executable instructions that, when executed, cause the one or more processors to perform an act comprising:

determining that the third ratio is approximately equal to one;

and wherein the determining the voltage or current value comprises determining the voltage or current value, from multiple voltage or current values, based at least in part on determining that the third ratio is approximately equal to one.

9. The eyeglass system as recited in claim 7, wherein the one or more computer-readable media further store computer-executable instructions that, when executed, cause the one or more processors to perform an act comprising:

determining that the third ratio is greater than one by a threshold amount;

and wherein the determining the voltage or current value comprises determining the voltage or current value, from multiple voltage or current values, based at least in part on determining that the third ratio is greater than one by the threshold amount.

10. The eyeglass system as recited in claim 3, wherein the one or more computer-readable media further store computer-executable instructions that, when executed, cause the one or more processors to perform acts comprising:

receiving, from the one or more sensors, second sensor data associated with the at least one eye;

determining, based at least in part on the second sensor data, a second target optical power for the first lens; and causing the power source to provide the second voltage or the second current value to the first lens.

11. The eyeglass system as recited in claim 3, wherein the one or more computer-readable media further store computer-executable instructions that, when executed, cause the one or more processors to perform acts comprising:

determining whether the user is looking at a distant object or a near object; and the determining the target optical power comprises determining the target optical power based at least in part on whether the user is looking at the distant object or the near object.

12. The eyeglass system as recited in claim 3, further comprising a temperature sensor, and wherein:

the one or more computer-readable media further store computer-executable instructions that, when executed, cause the one or more processors to perform an act comprising determining, using the temperature sensor of the eyeglass system, an ambient temperature; and the determining the voltage or current value is further based at least in part on the ambient temperature.

13. A method implemented at least in part by an eyeglass system, the method comprising:

generating sensor data by one or more sensors of the eyeglass system, the sensor data including image data representing a pupil and an edge of at least one eye of a user wearing the eyeglass system;

determining, based at least in part on the sensor data, a distance between the pupil and the edge of the at least one eye;

determining, based at least in part on the distance between the pupil and the edge of the at least one eye, a target optical power for one or more lenses of the eyeglass system;

determining, based at least in part on the target optical power, a voltage or current value; and instructing a power source of the eyeglass system to provide the voltage or current value to the one or more lenses.

14. The method as recited in claim 13, wherein the generating the sensor data comprises generating, by one or more cameras, the image data representing the pupil and the edge of the at least one eye of the user wearing the eyeglass system.

15. The method as recited in claim 13, further comprising:

generating additional sensor data by the one or more sensors;

determining, based at least in part on the additional sensor data, a new target optical power for the one or more lenses;

determining, based at least in part on the new target optical power, a new voltage or current value; and instructing the power source of the eyeglass system to provide the new voltage or current value to the one or more lenses.

16. The method as recited in claim 13, further comprising analyzing the sensor data to determine that the user wearing the eyeglass system is looking at a distant object, and wherein the target optical power is associated with the user looking at the distant object.

17. The method as recited in claim 13, further comprising analyzing the sensor data to determine that the user wearing the eyeglass system is looking at a near object, and wherein the target optical power is associated with the user looking at the near object.

18. The method as recited in claim 13, further comprising analyzing the sensor data to determine that the user wearing the eyeglass system is looking at a mid-range object, and wherein the target optical power is associated with looking at the mid-range object.

19. The method as recited in claim 13, further comprising analyzing the sensor data to determine data indicative of a convergence angle between a left eye and a right eye of the user wearing the eyeglass system, and wherein the target optical power is associated with the data indicative of the convergence angle.

20. The method as recited in claim 13, further comprising determining, using a temperature sensor of the eyeglass system, an ambient temperature, and wherein the determining the voltage or current value is further based at least in part on the ambient temperature.

* * * * *